United States Patent [19]

Ball et al.

[11] 4,376,104

[45] Mar. 8, 1983

[54] METHOD FOR PREPARING CRYSTALLINE ALUMINOSILICATES

[75] Inventors: William J. Ball, Capel; David G. Stewart, Epsom, both of England

[73] Assignee: The British Petroleum Company Limited, London, England

[21] Appl. No.: 276,522

[22] Filed: Jun. 23, 1981

Related U.S. Application Data

[63] Continuation-in-part of Ser. No. 101,843, Dec. 10, 1979, abandoned.

[30] Foreign Application Priority Data

Jan. 5, 1979 [GB] United Kingdom ............... 7900330

[51] Int. Cl.³ .......................................... C01B 33/28
[52] U.S. Cl. ............................. 423/329; 252/455 Z; 260/448 C; 423/328
[58] Field of Search ........................... 423/328–330; 252/431 N, 455 Z; 260/448 C

[56] References Cited

U.S. PATENT DOCUMENTS

| | | | |
|---|---|---|---|
| 3,506,400 | 4/1970 | Eberly et al. | 423/328 |
| 4,107,195 | 8/1978 | Rollmann | 423/329 X |
| 4,151,189 | 4/1979 | Rubin et al. | 260/448 C |
| 4,242,233 | 12/1980 | Ball | 423/329 X |

FOREIGN PATENT DOCUMENTS 1365318 8/1974 United Kingdom ............... 423/329

OTHER PUBLICATIONS

Voorhies "J. of Catalysis" 22, 1971, 419–426.

*Primary Examiner*—Edward J. Meros
*Attorney, Agent, or Firm*—Brooks, Haidt, Haffner & Delahunty

[57] ABSTRACT

Crystalline aluminosilicates having a high silica to alumina molar ratio are prepared by mixing a source of silica, a source of alumina, a source of alkali metal, water and one or more substituted neopentylamines having the formula:

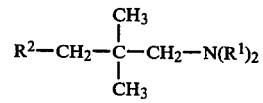

wherein $R^2$ is H, OH or $NH_2$ and $R^1$ is a $C_1$ to $C_6$ alkyl group, and maintaining the mixture under conditions of elevated temperature and pressure, typically in the range from 80° to 210° C. and autogenous pressure for a time sufficient to effect formation of the aluminosilicate, typically not less than 4 hours. The molar ratio of silica to alumina in the initial mixture is suitably in the range from 10:1 to 150:1 and the amounts of alkali metal and neopentylamine are suitably in the range from 2:1 to 0.02:1 and 10:1 to 0.02:1 respectively moles per mole equivalent of total silica and alumina in the respective sources. Depending on the ratio of silica to alumina in the initial mixture crystalline aluminosilicates having a mordenite structure or a ZSM-5 type zeolite structure or mixtures thereof may be prepared. Mordenites having a silica to alumina ratio greater than 10:1 can be prepared.

4 Claims, No Drawings

METHOD FOR PREPARING CRYSTALLINE ALUMINOSILICATES

This application is a continuation-in-part of application Ser. No. 101,843 filed on Dec. 10th 1979, now abandoned.

The present invention relates to a method for preparing crystalline aluminosilicates useful as catalyst supports and as conversion catalysts. More particularly this invention relates to a method for preparing crystalline aluminosilicates having a high silica to alumina ratio from a reaction mixture containing one or more substituted neopentylamines.

Aluminosilicates, both natural and synthetic, have been shown to contain a wide variety of positive ions. These aluminosilicates are rigid three-dimensional networks of $SiO_4$ and $AlO_4$ in which the tetrahedra are crosslinked by the sharing of oxygen atoms whereby the ratio of the total aluminium and silicon atoms of oxygen is 1:2. The electrovalence of the tetrahedra containing aluminium is balanced by the inclusion of a cation in the three dimensional structure. This cation in the initially formed aluminosilicate is generally an alkali metal.

Mordenite is a naturally occurring crystalline aluminosilicate zeolite found in nature in various forms such as sedimentary deposits at a number of locations in the United States, Japan and elsewhere. The typical unit cell content of the mineral, natural mordenite is given by the formula:

$$M_{8/n}[(AlO_2)_8(SiO_2)_{40}]24H_2O$$

wherein M is an alkali or alkaline earth metal cation or mixture thereof and n is the valence of the cation. As found in nature the molar ratio of $SiO_2$ to $Al_2O_3$ usually varies from about 8 to about 10. The silica to alumina ratio can be increased beyond 10 by a technique known in the art as "dealuminisation" which, as the name implies, is a treatment involving the removal of aluminium.

It has also been proposed to include in the aluminosilicate organic nitrogen cations notably quaternary ammonium cations such as tetramethylammonium, tetraethylammonium, tetrapropylammonium and tetrabutylammonium. Inorganic cations can be exchanged either in their entirety or partially by another type of cation utilising ion exchange techniques in a conventional manner. On the other hand, due to pore size limitations, organic cations are not necessarily susceptible to further cation exchange. In the hydrated form molecules of water occupy the spaces between the tetrahedra.

In the past, techniques of synthesising aluminosilicates have involved the use of solutions containing a source of silica, alumina, alkali metal and the cation in the form in which it would exist in the synthesised aluminosilicate. This method became rather expensive with the advent of crystalline aluminosilicates containing tetraalkylammonium cations. The synthesis of these aluminosilicates involved the addition of expensive quaternary ammonium cations to a reaction mixture in order to obtain the desired aluminosilicates. Furthermore, in order to exchange an ammonium or other cation into the aluminosilicate prior to producing the active form of the catalyst, it was necessary to calcine the aluminosilicate to decompose the quaternary ammonium cation.

A range of crystalline aluminosilicates having a "high", that is 10:1 or more, silica to alumina molar ratio, high stability, extremely high acidity, and the ability to catalyse many kinds of conversion reactions are prepared from one or more quaternary alkylammonium compounds in U.S. Pat. No. 3,702,886. The crystalline aluminosilicates prepared from tetrapropylammonium hydroxide in that patent were designated ZSM-5 zeolites and their X-ray diffraction patterns were given. Furthermore, a mordenite having a silica to alumina ratio greater than that found in naturally occurring mordenites, i.e. about 10:1, is prepared from tetraethylammonium bromide in Example 10 of British Patent Specification No. 1,554,955. In that Example a mordenite having a silica to alumina ratio of 30:1 is prepared by crystallising a mixture of a sodium aluminate solution, tetraethylammonium bromide and colloidal silica sol. The use of mordenites having silica to alumina ratios greater than about 15:1 as active catalysts for the conversion of methanol or methyl ethers to hydrocarbon mixtures is also described. However, the use of quaternary alkylammonium compounds is not without its disadvantages, not the least of which is their high cost. British Patent Specification No. 1,365,318 discloses an attempt to overcome this disadvantage by employing in the synthesis of aluminosilicates containing organic nitrogen cations such as ZSM-5 the precursors of the tetraalkylammonium compound i.e. $R_1R_2R_3N+R_4X$ in which $R_1$, $R_2$ and $R_3$ are selected from aryl, substituted aryl, alkyl, substituted alkyl, cycloalkyl, substituted cycloalkyl and hydrogen $R_4$ is alkyl, substituted alkyl, cycloalkyl, substituted cycloalkyl, aryl and substituted aryl and X is an electronegative group. This method only partially alleviates the expense problem and does not eliminate a further disadvantage associated with crystalline aluminosilicates prepared from tetraalkylammonium compounds, namely that in order to exchange an ammonium or other cation into the aluminosilicate preliminary to producing the active form it is necessary to calcine the aluminosilicate. For example, in Example 10 of GB Pat. No. 1,554,955 residual sodium is removed by heating the crystalline product in $N_2$ for 3 hours at 1,000° F. (i.e. calcining) and then exchanging with $NH_4Cl$ four times before recalcining for 10 hours at 1,000° F.

The disadvantages inherent in the aforesaid methods for synthesising crystalline aluminosilicates of the ZSM-5 type and in particular the high alkali metal content are purportedly overcome in British Pat. No. 1,471,440 which claims a method for synthesising a crystalline aluminosilicate zeolite containing an organic nitrogen cation, wherein a reaction mixture comprising sources of silica, alumina and alkali metal, water and a primary amine having 2 to 10 carbon atoms is prepared and maintained under conditions of temperature and pressure to effect crystallisation of said aluminosilicate zeolite. The Examples in the complete specification describe the use of a wide variety of primary amines in the preparation of crystalline aluminosilicates and the use of a few unsubstituted amines in the preparation of both crystalline and amorphous aluminosilicates.

In accordance with our invention it has been found that crystalline aluminosilicates having a high silica to alumina ratio can be prepared from a substituted neopentylamine or a mixture thereof and that the products so produced can be exchanged with an ammonium or other cation without prior calcination. Furthermore, the structure of the resulting crystalline aluminosilicate can be that of a mordenite or a ZSM-5 type zeolite depending on the ratio of silica to alumina in the initial reaction mixture.

According to the present invention there is provided a method for preparing a crystalline aluminosilicate having a high silica to alumina molar ratio which method comprises mixing a source of silica, a source of alumina, a source of alkali metal, water and at least one substituted neopentylamine according to Formula (I):

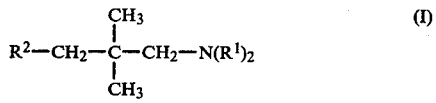

wherein $R^2$ is either hydrogen, an —OH group or an —NH$_2$ group and $R^1$ is an alkyl group containing from 1 to 6 carbon atoms, the ratio of said source of silica to said source of alumina being at least 10:1 based on the equivalent moles of silica and alumina in said respective sources, maintaining said mixture at elevated temperature and recovering the crystalline aluminosilicate formed.

Suitable sources of silica include, for example, sodium silicate, silica hydrosol, silica gel, silica sol and silicic acid. The preferred source of silica is an aqueous colloidal dispersion of silica particles. A suitable commercially available source of silica is LUDOX Colloidal Silica manufactured by DuPont (LUDOX is a Registered Trade Mark).

Suitable sources of alumina include, for example, sodium aluminate, aluminium sulphate and alumina. The preferred source of alumina is sodium aluminate prepared by dissolving alumina particles in excess sodium hydroxide solution.

Suitable sources of alkali metal include alkali metal hydroxides and alkali metal oxides. Preferably the alkali metal is sodium.

It will be appreciated that each source of silica, alumina and alkali metal can be supplied by one or more initial reactants and then mixed together in any order. For example, sodium silicate is a source of both sodium and silica.

In the formula (I) for the substituted neopentylamine, $R^2$ is either an —NH$_2$ or an —OH group or a hydrogen atom and $R^1$ is an alkyl group containing from 1 to 6 carbon atoms. Preferably $R^1$ is an alkyl group containing from 1 to 3 carbon atoms, even more preferably $R^1$ is a methyl group. Examples of suitable substituted neopentylamines having the formula (I) are dimethylamino neopentanamine (N,N,2, 2-tetramethylpropan-1, 3-diamine) and dimethylneopentanolamine (3-dimethylamino-2, 2-dimethylpropan-1-ol). Substituted neopentylamines having the formula (I) in which $R^3$ is —OH or —NH$_2$ and $R^1$ is methyl are supplied by BASF Aktiengesellchaft.

The elevated temperature may suitably be in the range from 80° to 210° C., preferably from 130° to 190° C.

As is well known in the art, the use of particularly advantageous conditions, such as seeding, i.e. the introduction of a small amount of the desired crystalline material, may allow the use of lower temperatures within the aforesaid ranges, or even lower temperatures if so desired. The pressure may suitably be autogenous pressure, that is the pressure generated at the temperature employed, though pressures above autogenous and as high as 400 psig may be used. Preferably the pressure may range from about autogenous to 250 psig. The mixture may suitably be maintained under the aforesaid conditions for a time not less than 4 hours, preferably at least 20 hours. Generally a time of about 48 hours will be found suitable though times up to and in excess of 7 days may be employed. Of course, the crystallisation time should not be so protracted that the crystalline aluminosilicate produced is converted to quartz.

The source of silica, alumina and alkali metal, water and secondary or tertiary amine of formula (I) or mixture thereof may be mixed in quite wide proportions. Thus the ratio of silica source to the alumina source may be in the range of from 10:1 to 150:1, preferably from 20:1 to 100:1, based on the equivalent moles of silica and alumina in the respective sources. The ratio of the number of moles of alkali metal to the number of mole equivalents of total silica and alumina in the sources of silica and alumina may be in the range from 2:1 to 0.02:1, preferably from 1:1 to 0.1:1. The ratio of the number of moles of neopentylamine of formula (I) to the number of mole equivalents of total silica and alumina in the sources of silica and alumina may suitable be in the range from 10:1 to 0.02:1, preferably from 10:1 to 0.1:1. Although the amounts of water present in the mixture is not critical to the performance of the invention, it is well known in the art that there must be sufficient water present to dissolve the reagents and not so much that the mixture is too dilute for crystallisation to occur.

The reaction is suitably carried out in a closed vessel capable of withstanding the elevated pressures generally employed. Furthermore the reaction mixture is preferably agitated during crystallisation of the aluminosilicate. The crystalline aluminosilicate so produced is preferably separated from the mother liquor by filtration and thereafter is preferably washed, suitably with water, at a temperature in the range, for example of from 15° to 95° C.

As mentioned hereinbefore, a feature of the process of the present invention is that the crystalline structure of the aluminosilicate produced thereby can be varied by altering the silica to alumina ratio in the initial mixture. At a silica to alumina ratio of about 15:1 in the initial mixture it is established from the X-ray powder diffraction pattern that the resulting crystalline aluminosilicate is a mordenite having a silica to alumina ratio greater than about 15:1 and at a ratio of about 60:1 in the initial mixture the resulting aluminosilicate is a ZSM-5, as described in U.S. Pat. No. 3,702,886 and UK Patent Specification No. 1,161,974. At a silica to alumina ratio of about 30:1 in the initial mixture a 50/50 mixture of the two crystalline forms is produced.

The recovered crystalline aluminosilicate may be used as a catalyst or as a catalyst support. It may be used on its own or admixed with up to 80% by weight of another support material such as silica, alumina or an aluminosilicate.

Before use as a catalyst or a catalyst support it is desirable to modify the crystalline aluminosilicate in one or a number or ways. Thus, for many catalytic purposes it is preferred to convert the aluminosilicate to the hydrogen form. This may suitably be achieved by subjecting the aluminosilicate to ion-exchange with a solution containing ammonium cations and calcining the resulting ammonium-exchanged material. Before ion-exchange it may be preferable to treat the aluminosilicate with a solution of an acid, e.g. an aqueous mineral acid. The hydrogen form of the aluminosilicate may be further exchanged with metal cations using conventional ion-exchange techniques. Before catalytic use it is preferred to activate the aluminosilicate, suitably by heating in air at a temperature in the range 400° to 700° C. for a period of from 2 to 48 hours.

Furthermore the aluminosilicate may be impregnated with a compound of one or more metals, preferably with a compound of one or more metals belonging to Groups 1B, 11B, 111A, 1VA, VA or V111 of the Periodic Table of the Elements as published in the Handbook of Chemistry and Physics, published by the Chemical Rubber Publishing Co. Suitable metals include copper, silver, zinc, gallium, indium, thallium, lead, antimony, bismuth, iron, cobalt, nickel, ruthenium, rhodium, palladium, iridium and platinum. The impregnated aluminosilicate preferably contains from 0.1 to 5.0% by weight of the metal(s). The compounds of the metals used are suitably those compounds which will decompose on the application of heat to form the corresponding oxides and which are soluble in water, eg the nitrates or chlorides. The aluminosilicates may thus be impregnated with an aqueous solution of a compound of the desired metal and the impregnated mass thereafter calcined to produce the metal oxide 'in situ' deposited in the interstices of the aluminosilicate structure. Alternatively or in addition the metal or metals may be incorporated by ion-exchange. In a further embodiment of the invention the aluminosilicate employed additionally contains one or more non-metallic elements belonging to Groups 111A and VA of the Periodic Table, especially boron and phosphorous. The non-metallic element may be incorporated into the aluminosilicate by reaction with a suitable compound containing the non-metallic element, eg phosphoric acid, trimethyl-phosphate or phosphorus trichloride, followed by heating. The amount of the non-metallic element present in the impregnated aluminosilicate preferably ranges from 0.1 to 5.0% by weight.

The aluminosilicates so-prepared, with or without the hereinbefore described treatments and/or modifications, may be used as catalysts in the form of a fixed or a fluidised bed in alkylation, dehydrocyclodimerisation, oligomerisation, isomerisation and hydrogenation reactions. Additionally the aluminosilicates may be used as catalysts in the dehydration of alcohols and ethers.

The following Examples are given for the purpose of illustrating the invention.

In the Examples reference will be made to the following:

X-RAY DIFFRACTION (XRD) PATTERNS

These were determined by a technique based on the method described in "X-Ray Diffraction Procedures. For Polycrystalline and Amorphous Materials" by H. P. Klug and L. E. Alexander, 2nd Edition, published by John Wiley & Sons, New York-London. Copper K-alpha radiation of wavelength 1.54084 Angstroms was used and the diffraction patterns were recorded on a strip chart recorder. Bragg angles were read from the chart and converted to d-spacings in Angstrom units. Peak heights were measured and normalised so that the strongest peak had a value of 100.

ELEMENTAL COMPOSITION (i) Silicon and aluminium

Silicon and aluminium were determined by X-ray fluorescence analysis (XRF) using a method based on that described in "Advances in X-ray Analysis" by F. Claisse and C. Samson, 1961, Vol. 5, page 335, published in New York by Plenum.

(ii) Sodium

Sodium was determined by atomic absorption spectroscopy (AAS) using a method based on that described in "Analytical Atomic Absorption Spectorscopy" by W. J. Price, published in London, New York and Rheine by Heyden & Son Limited.

PREPARATION OF ALUMINOSILICATES

EXAMPLE 1

Alumina, Laporte Type A (1.7 g) was dissolved in a hot solution of sodium hydroxide (2.6 g) in deionised water (25 ml). To this was added a mixture of Ludox colloidal silica (50 g, containing 30% silica) in a solution of 3-dimethylamino-2,2-dimethylpropan-1-ol (31.2 g) dissolved in deionised water (75 ml).

The resultant mixture was then placed in a revolving stainless steel pressure vessel and heated at 170° C. for 66 hours. The resultant solid product was filtered and washed with deionised water (1000 ml). The filter-cake was suspended in an aqueous solution of ammonia (150 ml 910 ammonia solution/150 ml deionised water) and stirred for one hour. The mixture was filtered and the solid washed with deionised water (500 ml). After washing the aluminosilicate so-prepared was dried at 120° C. for 16 hours. It was found to have a silica to alumina ratio of 17:1 and a sodium content of 0.02% b.w.

The crystalline aluminosilicate product was calcined at 500° C. in air for 16 hours.

The X-ray diffraction pattern for the calcined crystalline product is given in the following Table 1.

The structure was identified as that of mordenite by reference to data in the JCPDS Power Diffraction File.

EXAMPLE 2

Alumina, Laporte Type A (0.85 g) was dissolved in a hot solution of sodium hydroxide (2.6 g) in deionised water (25 ml).

This was added a mixture of Ludox colloidal silica (50 g, containing 30% silica) in a solution of 3-dimethylamino-2,2-dimethylpropan-1-ol (31.2 g) dissolved in deionised water (75 ml). The resultant mixture was placed in a revolving stainless steel pressure vessel and heated at 170° C. for 66 hours. The aluminosilicate was then processed as described in Example 1.

Analysis of the product by X-ray diffraction analysis after calcination at 500° C. for 16 hours in air showed it to be a 50/50 mixture of a ZSM-5 type zeolite and a mordenite.

EXAMPLE 3

Alumina, Laporte Type A (0.43 g) was dissolved in a hot solution of sodium hydroxide (2.6 g) in deionised water (25 ml). To this was added a mixture of Ludox colloidal silica (50 g, containing 30% silica) in a solution of 3-dimethylamino-2,2-dimethylpropan-1-ol (31.2 g) dissolved in deionised water (75 ml). The resultant mixture was placed in a revolving stainless steel pressure vessel and heated at 170° C. for 66 hours. The aluminosilicate was then processed as described in Example 1.

X-ray diffraction analysis of the aluminosilicate after calcining at 500° C. for 16 hours in air showed it to be a ZSM-5 type zeolite. The X-ray diffraction pattern is given in the following Table 2.

EXAMPLE 4

Alumina, Laporte Type A (1.7 g) was dissolved in a hot solution of sodium hydroxide (2.6 g) in deionised water (25 ml). To this was added a mixture of Ludox colloidal silica (50 g, containing 30% silica) in a solution of N, N, 2, 2-tetramethylpropan-1, 3-diamine (30.9 g) dissolved in deionised water (75 ml).

The resultant mixture was then placed in a revolving stainless steel pressure vessel and heated at 170° C. for 66 hours. The resultant solid product was filtered and washed with deionised water (1,000 ml).

The filter-cake was suspended in an aqueous solution of ammonia (200 ml 910 ammonia solution/200 ml deionised water) and stirred for 1 hour. The mixture was filtered and the solid washed with deionised water (400 ml). After washing the aluminosilicate so-prepared was dried at 120° C. for 16 hours. Its silica to alumina ratio was found to be 17:1 and its sodium content was 0.02% b.w.

The aluminosilicate was calcined at 500° C. in air for 16 hours. The X-ray diffraction pattern for the calcined crystalline product was substantially the same as that shown in Table 1. The structure was identified as that of mordenite by reference to data in the JCPDS Powder Diffraction File.

TABLE 1

X-Ray Powder Diffraction Data

| | Example 1 | | | Example 4 | | |
|---|---|---|---|---|---|---|
| h k l | $2\theta$ | I | d | $2\theta$ | I | d |
| 110 | 6.47 | 40 | 13.66 | 6.44 | 40 | 13.72 |
| 020 | 8.62 | 25 | 10.26 | 8.63 | 20 | 10.25 |
| 200 | 9.47 | 100 | 9.08 | 9.47 | 100 | 9.08 |
| 111 | 13.44 | 60 | 6.59 | 13.44 | 60 | 6.59 |
| 130 | 13.87 | 15 | 6.38 | 13.86 | 15 | 6.39 |
| 021 | 14.62 | 10 | 6.06 | 14.60 | 10 | 6.07 |
| 310 | 15.43 | 25 | 5.74 | 15.20 | 25 | 5.83 |
| 330 | 19.62 | 45 | 4.52 | 19.58 | 45 | 4.53 |
| 150 | 22.32 | 75 | 3.98 | 22.28 | 75 | 3.99 |
| 241 | 23.23 | 15 | 3.83 | 23.22 | 20 | 3.83 |
| 002 | 23.70 | 10 | 3.75 | 23.68 | 10 | 3.76 |
| 202 | 25.48 | 100 | 3.50 | 25.66 | 90 | 3.47 |
| 060 | 26.33 | 55 | 3.38 | 26.29 | 55 | 3.39 |
| 530 | 27.78 | 55 | 3.21 | 27.65 | 55 | 3.23 |
| 531 | 30.50 | 5 | 2.93 | 30.50 | 5 | 2.93 |
| 402 | 30.95 | 25 | 2.89 | 30.92 | 20 | 2.89 |

TABLE 2

| 2-Theta | d(Å) | Relative Intensities I/Io | 2-Theta | d(Å) | Relative Intensities I/Io |
|---|---|---|---|---|---|
| 6.96 | 12.70 | 3 | 22.94 | 3.88 | 95 |
| 7.79 | 11.35 | 94 | 23.14 | 3.84 | 70 |
| 8.12 | 10.89 | 5 | 23.55 | 3.78 | 33 |
| 8.70 | 10.16 | 56 | 23.76 | 3.75 | 40 |
| 8.95 | 9.88 | 17 | 24.23 | 3.67 | 31 |
| 9.46 | 9.85 | 4 | 25.39 | 3.51 | 3 |
| 9.61 | 9.20 | 6 | 25.60 | 3.48 | 11 |
| 11.76 | 7.53 | 3 | 25.73 | 3.46 | 9 |
| 13.04 | 6.79 | 6 | 26.48 | 3.37 | 100 |
| 13.36 | 6.68 | 5 | 26.76 | 3.33 | 12 |
| 13.76 | 6.49 | 13 | 27.10 | 3.29 | 4 |
| 14.46 | 6.13 | 8 | 27.28 | 3.27 | 5 |
| 14.65 | 6.05 | 14 | 27.42 | 3.25 | 5 |
| 15.13 | 5.86 | 3 | 27.45 | 3.29 | 4 |
| 15.38 | 5.76 | 9 | 27.82 | 3.21 | 3 |
| 15.75 | 5.63 | 12 | 28.25 | 3.16 | 3 |
| 17.52 | 5.06 | 6 | 28.61 | 3.12 | 9 |
| 17.67 | 5.02 | 6 | 29.12 | 3.07 | 9 |
| 17.97 | 4.94 | 3 | 29.69 | 3.01 | 10 |
| 19.09 | 4.65 | 6 | 29.83 | 3.00 | 11 |
| 19.46 | 4.56 | 3 | 30.19 | 2.96 | 7 |
| 20.18 | 4.40 | 3 | 31.04 | 2.88 | 3 |
| 20.70 | 4.29 | 28 | 31.38 | 2.85 | 4 |
| 22.03 | 4.04 | 15 | | | |

Use of aluminosilicates as catalysts in the conversion of methanol into hydrocarbons

EXAMPLE 5

Equal weights of the aluminosilicate product of Example 1 and Ludox colloidal silica (containing 30% silica) were mixed together in the presence of deionised water and dried at 120° C. The mixture was then broken down to pass 5–8 mesh (BSS) and activated by heating in air at 500° C. for 16 hours.

The catalytic activity of the activated aluminosilicate/silica mixture was tested by passing a gaseous feed of methanol over the mixture contained in a heated glass reactor. The reaction conditions, the yields of ethylene, $C_3$ and $C_4$ hydrocarbons obtained therefrom and the methanol conversion after 30 minutes on stream are given in the following Table 2.

EXAMPLE 6

The procedure of Example 5 was followed except that the aluminosilicate product of Example 2 was used in place of that of Example 1. The results are given in the following Table 2.

EXAMPLE 7

The procedure of Example 5 was followed except that the aluminosilicate product of Example 3 was used in place of that of Example 1. The results are given in the following Table 2.

EXAMPLE 8

The procedure of Example 5 was followed except that the aluminosilicate of Example 4 was used in place of that of Example 1. The results are given in the following Table 2.

TABLE 3

| Example | Contact time (secs at NTP)* | Reaction temperature (°C.) | % Yield on methanol fed** | | | Recovered*** methanol + dimethylether |
|---|---|---|---|---|---|---|
| | | | $C_2$ | $C_3$ | $C_4$ | |
| 5 | 3.0 | 400 | 4 | 6 | 5 | 54 |
| 6 | 2.3 | 400 | 5 | 19 | 30 | Nil |
| 7 | 1.8 | 400 | 6 | 20 | 30 | Nil |
| 8 | 3.0 | 400 | 16 | 25 | 3 | TRACE |

*The contact time is defined as: $\frac{\text{Volume of catalyst in mls}}{\text{Total volume of gas (in mls/sec at NTP)}}$

**The % yield of $C_2$ hydrocarbons on methanol fed is defined as: $\frac{\text{Moles of methanol converted to } C_2}{\text{Total moles of methanol fed}}$ The % yield of $C_3$ and $C_4$ hydrocarbons is defined in a similar manner

***The remaining products were a complex mixture of straight- and branched-chain hydrocarbons and aromatics containing significant amounts of penta- and hexa methyl benzenes.

We claim:

1. A method for preparing a crystalline aluminosilicate having a high silica to alumina molar ratio which method comprises mixing a source of silica, a source of alumina, a source of alkali metal, water and at least one substituted neopentylamine according to Formula (I):

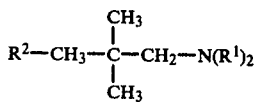

wherein $R^2$ is either —OH or —NH$_2$ and R' is an alkyl group containing from 1 to 6 carbon atoms, the ratio of said source of silica to said source of alumina being at least 10:1 based on the equivalent moles of silica and alumina in said respective sources, maintaining said mixture at elevated temperature and recovering the crystalline aluminosilicate so formed.

2. A method according to claim 1 wherein in said Formula (I) $R^2$ is either —OH or —NH$_2$ and $R^1$ is methyl.

3. A method according to claim 1 wherein said substituted neopentylamine of Formula (I) is N,N,2,2-tetramethylpropan-1,3-diamine.

4. A method according to claim 1 wherein said substituted neopentylamine of Formula (I) is 3-dimethylamino-2,2-dimethylpropan-1-ol.

* * * * *

UNITED STATES PATENT AND TRADEMARK OFFICE
CERTIFICATE OF CORRECTION

PATENT NO. : 4,376,104
DATED : March 8, 1983
INVENTOR(S) : WILLIAM J. BALL and DAVID G. STEWART It is certified that error appears in the above—identified patent and that said Letters Patent is hereby corrected as shown below:

Col. 1, line 20, after "atoms" and before "oxygen", change "of" to --to--.

Col. 2, line 62, after "unsubstituted" and before "amines", insert --secondary--.

Col. 3, line 60, "130°" should read --135°--

Col. 6, line 39, after "JCPDS" change "Power" to --Powder--.

Signed and Sealed this

Third Day of January 1984

[SEAL]

Attest:

GERALD J. MOSSINGHOFF

Attesting Officer   Commissioner of Patents and Trademarks